United States Patent [19]
Gustilo

[11] Patent Number: 5,725,595
[45] Date of Patent: Mar. 10, 1998

[54] CANNULATED CEMENTLESS HIP STEM PROSTHESIS

[75] Inventor: Ramon B. Gustilo, Eden Prairie, Minn.

[73] Assignee: Orthopaedic Innovations, Inc., Minneapolis, Minn.

[21] Appl. No.: 603,408

[22] Filed: Feb. 20, 1996

Related U.S. Application Data

[63] Continuation of Ser. No. 335,678, Nov. 8, 1994, abandoned.

[51] Int. Cl.$^6$ ........................................... A61F 2/32
[52] U.S. Cl. ........................................... 623/23
[58] Field of Search ........................... 623/16, 18, 19, 623/22, 23

[56] References Cited

U.S. PATENT DOCUMENTS

| | | | |
|---|---|---|---|
| 4,287,617 | 9/1981 | Tornier | 623/23 |
| 4,770,660 | 9/1988 | Averill | 623/23 |
| 4,775,381 | 10/1988 | Tari et al. | 623/23 |
| 4,808,186 | 2/1989 | Smith | 623/23 |
| 4,851,007 | 7/1989 | Gray | 623/23 |
| 4,919,673 | 4/1990 | Willert et al. | |
| 4,921,501 | 5/1990 | Giacometti | 623/23 |
| 4,944,759 | 7/1990 | Mallory et al. | 623/22 |
| 5,015,817 | 5/1991 | Kranz | |
| 5,047,035 | 9/1991 | Mikhail et al. | 623/23 |
| 5,078,746 | 1/1992 | Garner | |
| 5,152,798 | 10/1992 | Kranz | |
| 5,163,961 | 11/1992 | Harwin | 623/23 |
| 5,201,770 | 4/1993 | Sola | 623/23 |
| 5,316,550 | 5/1994 | Forte | 623/23 |

*Primary Examiner*—Debra S. Brittingham
*Attorney, Agent, or Firm*—Gregory F. Cotterell

[57] ABSTRACT

The present invention includes a cannulated hip stem prosthesis for implantation in a living femur. The cannulated prosthesis terminates in a flexible distal portion. The cannulated prosthesis includes an interstitial surface for promoting bone cell ingrowth.

21 Claims, 2 Drawing Sheets

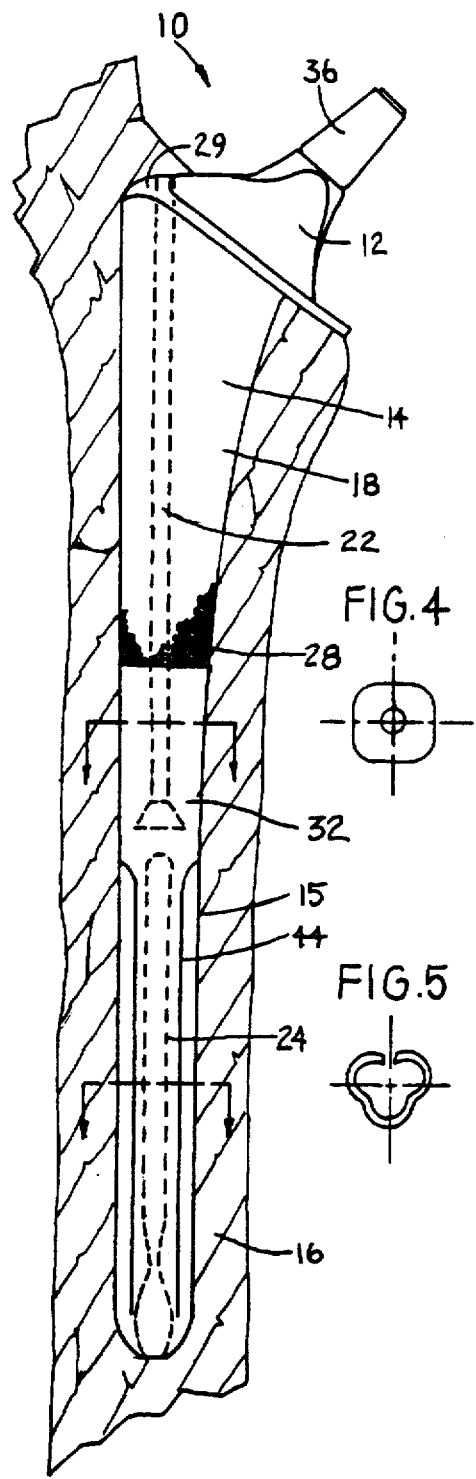
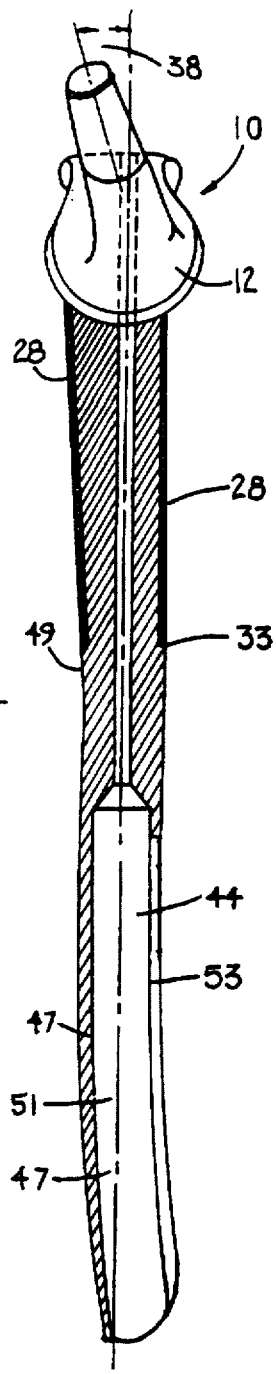
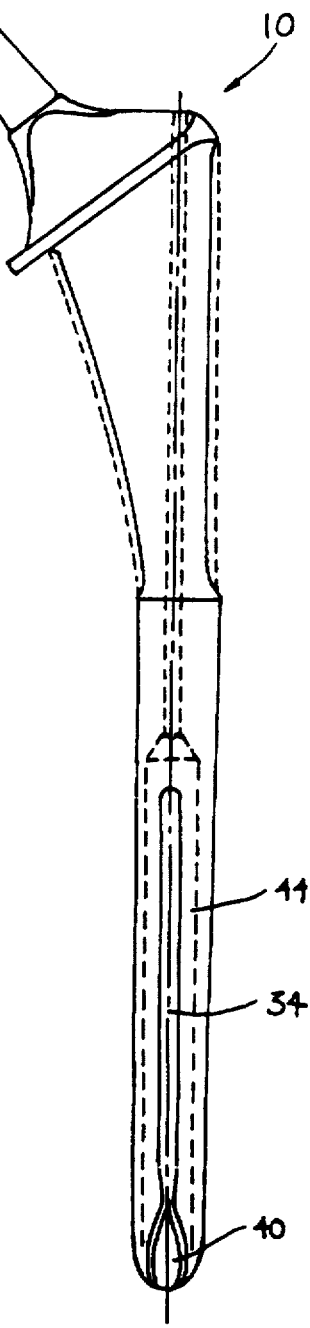

CANNULATED CEMENTLESS HIP STEM PROSTHESIS

This is a continuation of prior application Ser. No. 08/335,678, filed Nov. 8, 1994, now abandoned.

BACKGROUND OF THE INVENTION

The present invention relates to a cannulated cementless hip stem component of a hip prosthesis.

Implantation of a hip prosthesis requires that a surgeon initially excise a diseased or severely damaged femoral head, femoral neck, and re-shape a femoral shaft. The femoral components are replaced in whole or in part with the hip prosthesis. The hip prosthesis must be anchored and secured to the remaining portions of a patient's leg.

Typically, surgeons have taken two approaches in integrating the hip prosthesis into the patient's body. In a first approach, a living femur of the patient is reamed and broached. The femur is reamed to an inside diameter large enough to permit a mantle of bone cement to surround and embed a femoral stem prosthesis. The femoral stem prosthesis is then positioned and centered in the mantle of bone cement which acts as a grouting agent between the femoral stem prosthesis and the cemented living bone. It is important that the cement mantle surround and embed the femoral stem because it is the cement that must support the prosthesis and absorb every day stresses placed on the prosthesis by the patient.

In a second approach, a surgeon carefully reams the living femoral bone tissue of the patient to a degree that permits the femoral stem prosthesis to fit snugly in a canal prepared by reaming. The femoral stem prosthesis directly and intimately contacts the living bone. It is important that the femoral prosthesis be positioned in the living femur in a manner to promote uniform distribution of stresses and load between the living femur and the femoral prosthesis.

SUMMARY OF THE INVENTION

The present invention includes a cannulated hip stem prosthesis for implantation in a living femur. The cannulated prosthesis terminates in a flexible distal portion. The cannulated prosthesis includes an interstitial surface for promoting bone cell ingrowth.

The present invention also includes a process for improving load and stress distribution in a hip stem implant that contacts a living femur. The process includes providing a cannulated implant terminating in a flexible distal portion. The implant includes an interstitial surface. The hip stem prosthesis is precisely positioned in the femur with a guide rod. The interstitial surface contacts the living femur.

DESCRIPTION OF THE DRAWINGS

FIG. 1 is a front elevational view of one embodiment of the hip stem prosthesis of the present invention when inserted into a living femur show in cross section.

FIG. 2 is a medial side elevational view of the hip stem prosthesis embodiment of FIG. 1.

FIG. 3 is a rear elevational view of the hip stem prosthesis embodiment of FIG. 1.

FIG. 4 is an axial cross-sectional view of one section of the femoral prosthesis at the corresponding level indicated in FIG. 1.

FIG. 5 is an axial cross-sectional view of a second section of the femoral prosthesis at the corresponding level indicated in FIG. 1.

DESCRIPTION OF PREFERRED EMBODIMENTS

Figure 6:
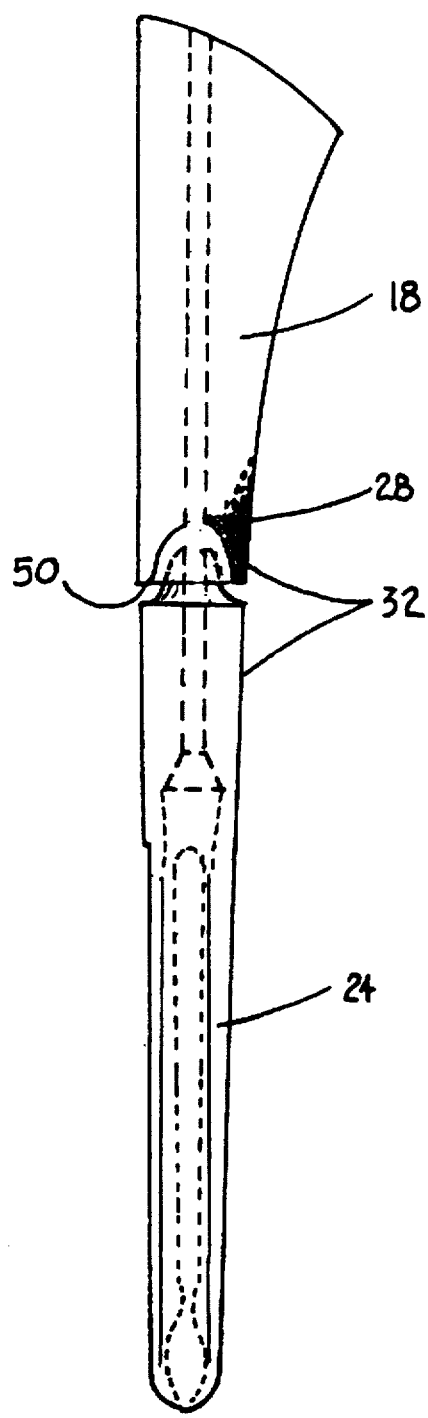
FIG. 6 is a front elevational view of on embodiment of the present invention showing modular proximal and distal components of the distal stem of the hip stem prosthesis.

The hip stem prosthesis of the present invention illustrated generally at 10 in FIG. 1, includes a collar component 12 attached to a cannulated femoral stem component 14. The cannulated femoral stem component 14 includes a flexible distal section 24, a proximal section 18 having an interstitial surface 28, and a transitional section 32 conjoining the flexible distal section 24 and the proximal section 18. The cannulated femoral stem component 14 encloses a canulae 22 that extends from a proximal end 29 to the flexible distal section 24 of the prosthesis 10. By "distal section" is meant, a section of the stem component 14 farthest away from the collar component 12. By "proximal section" is meant a section of the femoral stem component 14 that is adjacent to the collar component 12. The proximal section is proximal to a trunk of a body of a living being.

In one preferred embodiment, the flexible distal section 24, proximal section 18 and transitional section 32 are part of a unitary femoral stem component 14. In one other embodiment illustrated in FIG. 6, the flexible distal section 24 and proximal section 18 are separate modular components that are conjoined at the transitional section 32. The modular components may be sized for different stem lengths. The components may be attached by a taper joint 50. The cannulated femoral stem component 14 is positioned within an intramedullary canal 15 of a living femur 16 and is flush with the living femoral bone 16.

The hip stem prosthesis 10 of the present invention is a great improvement over existing femoral prostheses because the hip stem prosthesis of the present invention 10 includes features that optimize positioning of the prosthesis and better distribute load and load related stresses over the prosthesis 10 and living femoral tissue 16. The improved load distribution occurs because of a combination of factors. First, the canulae feature 22 of the stem component 14 permits the stem to be precisely aligned in the intramedullary canal 15, along a guide rod (not shown) passing through the canulae 22 during installation.

Second, the flexible distal section 24 is open and is easier to position in the intramedullary canal 15 than other prosthesis. Also, the flexible distal section 24 has an axial cross-sectional symmetry, illustrated at 30 in FIG. 5, that deflects load and other stresses away from the prothesis 10 and into the natural femoral bone 16. Consequently, the hip stem prosthesis 10 has a more balanced and natural load distribution over the distal stem component 14.

Third, the hip stem prosthesis 10 of the present invention is better able to deflect and bear load as conditions require because the prosthesis 10 interacts with the living femoral bone 16. As discussed, the cannulae feature 22 of the prosthesis 10 and flexibility of the open distal section 24 aid in precise alignment of the prosthesis 10 that is substantially flush with the bone 16. Additionally, the outer surface of the prosthesis 10 is roughened or "enhanced" to form an interstitial surface, a surface area illustrated at 28 in FIGS. 1 and 2. This roughened, interstitial surface is most preferably located proximally on the stem 14 extending about the perimeter of the stem 14 one-third to two-thirds of the length of the femoral stem component 14. The interstitial surface 28 is proximal to the collar 12 and is located in the proximal section 18. It has surprisingly been found that the prosthesis 10 optimally interacts with living bone 16 at the interstitial surface 28 when the surface 28 is in the one-third to two-thirds length position.

It is believed that the combination of the prosthesis 10 enclosing the cannulae 22, the prosthesis 10 having a flexible and open distal section 24, and the prosthesis 10 having an interstitial surface 28 in the proximal section 18, makes an implant that is synergistically better than an implant having any single feature. It is believed that the combination of these three features of the implant of the present invention acts synergistically to make a hip stem prosthesis 10 that can be precisely positioned and that can deflect and bear load in a dynamic manner corresponding to a natural femoral bone. The cannulation feature 22 of the hip stem prosthesis 10 permits the prosthesis to be precisely centered and positioned along a guide rod when positioned within the intramedullary canal 15. The precise positioning of the interstitial surface 28 promotes bone ingrowth in accordance with load distribution along the implant. The flexible, open distal section 24 as well as the cannulae 22 confer a property of flexibility to the implant that makes the implant easier to position within the intramedullary canal 15. The flexible distal section 24 also deflects stresses and load into the natural bone in a manner that is a great improvement over existing hip stem prostheses.

In one embodiment, the interstitial surface 28 is roughened by sintering. However, it is contemplated that the interstitial surface 28 may be roughened by other methods that roughen metal surfaces including casting, bead blasting, plasma spray and other conventional methods.

The interstitial surface 28 may also be formed by coating the surface. The coating may include an interstitial metal coating. In one embodiment, beads of cobalt-chromium are applied to the proximal section of the femoral stem component 18 to make the interstitial surface 28. In one preferred embodiment, several layers of beads are applied to the surface 28 in order to create the network of interstices as is shown in FIG. 1. The coating may also include a biological coating. The biological coating may include hydroxyapatite to promote bony ingrowth. The interstitial surface 28 may also be formed by a combination of roughening the surface and coating the surface.

The network of interstices roughening the surface 28 greatly increases the surface area of the femoral stem component 14. By increasing the surface area in this manner, the surrounding bone 16 is provided with a large surface area in which the bone tissue can grow into the interstices thereby bonding with the prosthesis 10. Over time then, a boundary between the hip stem prosthesis 10 and the living bone 16 becomes indistinct and dynamic. The living bone 16 may be alternately concentrated or resorbed from point-to-point, along the hip stem prosthesis 10 over time, in response to particular local stresses and loads. As a consequence, load and stress are more naturally distributed about the fused structure of femoral stem component 14 and living bone 16 than for a femoral stem lacking such a dynamic bond.

Typically, the hip stem prosthesis 10 is made of a material such as titanium, a cobalt-chromium alloy, stainless steel or other material of a surgical grade suitable for implantation.

The transitional section 32 is distally positioned with respect to the interstitial surface 28. In one embodiment, the transitional section 32 has a rectangular cross-section and rounded corners 33.

The flexible distal section 24 of the stem component 14 is defined by a slotted shell 44 that encloses a space 34, illustrated in FIG. 3. As discussed, the flexible distal section 24 is lightweight, thereby minimizing unnatural, undesirable stress on the hip stem prosthesis 10 and living bone 16.

In one preferred embodiment, the shell 44 of the flexible distal section 24 has an open tripolar shape 40, as illustrated in FIG. 3 and in cross-section in FIG. 5. The tripolar shell 40 is made of a material such as titanium or cobalt chromium. The tripolar shell 40 is positioned posterior and opposing an anterior curve 47 of the distal stem component 14 to preserve bending and torsional strength of the stem 14.

The distal stem component 14 of the prosthesis 10 has an asymmetric shape that optimizes bony ingrowth and stress deflection. The prosthesis 10 has a lateral border 49 that is substantially straight. The prosthesis 10 also has an anterior surface 51 with the anterior curve 47 that follows the symmetry of the natural bone. The prosthesis 10 also has a posterior surface 53 that is asymmetrical with respect to the anterior surface 51. Preferably, the open distal section 24 is curved in an anterior orientation illustrated in FIG. 2, in an arc of about 4 to 5 degrees.

The collar component 12 of the hip stem prosthesis 10 includes the femoral neck 36 attachable to a femoral head prosthesis (not shown). While the collar component 12 is described, it is understood that the prosthesis 10 may be made without a separate collar component 12. The collar component 12 may then be attachable to the stem component by a conventional mechanism that produces a snug fit between the collar component 12 and the stem component. It is also contemplated that the collar 12 and stem component may be formed as a single unitary prosthetic piece.

The femoral head prosthesis fits within an acetabulum (not shown). The femoral neck 36 is anteverted to form two angular relationships with the femoral shaft 14 that are important to hip joint function. The first angular relationship is an angle of inclination of the neck 36 to the stem 14 in a frontal plane, a neck-to-shaft angle.

A second angle of inclination is formed as a projection of a long axis of the natural femoral head and a transverse axis of natural femoral condyles. In adults, this angle is about 12 degrees but may vary a great deal. An angle greater than about 12 degrees causes a portion of the femoral head to be uncovered with respect to the acetabular cavity (not shown) and creates a tendency toward internal rotation of the leg during gait to keep the femoral head in the acetabular cavity. An angle less than 12 degrees produces a tendency toward external rotation of the leg during gait.

The prosthesis 10 is insertable in an intramedullary canal 15 of a femur once the femur has been prepared. First, an intramedullary guide such as a rod is positioned in the medullary canal. Then, the surgeon resects the femoral head and neck of the patient. The medullary canal is then reamed with a taper cannulated reamer, about 1-to-2 centimeters distal of a selected femoral component. The femur is then proximally rasped with a cannulated rasp. Next, the guide rod is removed and a trial reduction and tests for range of motion and leg length are performed using the rasp as a trial prosthesis. To insert the prosthesis, the rasp is removed from the canal, and the prosthesis 10 is positioned on the rod through the cannulae 22 of the prosthesis 10. Once the implant is positioned in the medullary canal, the rod may be removed.

Although the present invention has been described with reference to preferred embodiments, workers skilled in the art will recognize that changes may be made in form and detail without departing from the spirit and scope of the invention.

I claim:

1. A femoral stem component of a femoral hip prosthesis having an anterior surface, a posterior surface, a medial surface, a lateral surface, and a proximal pole generally opposite a distal pole along a longitudinal axis, the prosthesis generally wider medially proximate the proximal pole and suitable for implantation in a living being, the femoral stem component comprising:

a proximal portion including the proximal pole and a centrally located cylindrical bore open proximate the proximal pole and generally aligned along the longitudinal axis of the prosthesis suitable for slidably and telescopically receiving an aligning rod therethrough;

a transition portion, distal to the proximal portion, including a centrally located cavity aligned along the longitudinal axis, the cavity having a shape generally narrow proximally and substantially wider distally resulting from thinning of the stem wall, the cavity in open communication with the cylindrical bore proximally; and a flexible shell portion, distal to the transition portion and including the distal pole, the flexible shell portion including a centrally located shell cavity, an opening into the shell cavity proximate the distal pole, and a longitudinally oriented slot in open communication with the shell cavity and the opening, the shell cavity in open communication with the transition portion cavity proximally;

wherein the transition portion and slotted flexible shell provide for a femoral stem component that is substantially flexible distally proximate the flexible shell relative to the proximal portion.

2. The femoral stem component of claim 1 further including an interstitial surface extending about a perimeter of the proximal portion.

3. The femoral stem component of claim 2 wherein the interstitial surface includes a coating bonded to the femoral stem component.

4. The femoral stem component of claim 2 wherein the interstitial surface includes coating with a material suitable for promoting a bony ingrowth.

5. The femoral stem component of claim 2 wherein the interstitial surface includes a sintered surface.

6. The femoral stem component of claim 2 wherein the interstitial surface covers between about one-third to about two-thirds of the surface of the stem prosthesis.

7. The femoral stem component of claim 1 further comprising a collar attachable to the proximal portion.

8. The femoral stem component of claim 1 further comprising a collar that is integral with the proximal portion.

9. The femoral stem component of claim 1 wherein the flexible shell portion includes a cross-sectional tripolar scalloped surface shape.

10. The femoral stem component of claim 1 wherein the flexible shell portion includes a short segment of narrowing proximate the distal pole.

11. The femoral stem component of claim 1 wherein the flexible shell portion includes a curving arc segment relative to the longitudinal axis.

12. A femoral stem component of a femoral hip prosthesis, suitable for implantation within a human patient, having an anterior surface, a posterior surface, a medial surface, a lateral surface, and a proximal pole generally opposite a distal pole along a longitudinal axis, the prosthesis generally wider medially proximate the proximal pole, the femoral stem component comprising:

a proximal component detachable from and operably interconnectable with a distal component at complimentary first and second mating surfaces;

the proximal component including the proximal pole, a centrally located cylindrical bore open proximate the proximal pole and generally aligned along the longitudinal axis of the prosthesis suitable for slidably and telescopically receiving an aligning rod therethrough; and the distal component comprising a transition portion proximal to a flexible shell;

the transition portion having the second mating surface proximate a proximal end, a centrally located cylindrical bore open proximate the proximal end and generally aligned along the longitudinal axis of the prosthesis suitable for slidably and telescopically receiving the aligning rod therethrough and distally opening into a centrally located cavity aligned along the longitudinal axis having a shape generally narrow proximally and substantially wider distally; and the flexible shell including the distal pole, a centrally located shell cavity, an opening into the shell cavity proximate the distal pole, and a longitudinally oriented slot in open communication with the shell cavity and the opening, the shell cavity in open communication with the transition portion cavity proximally;

wherein the transition portion and slotted flexible shell provide for a distal component that is substantially flexible relative to the proximal component.

13. The femoral stem component of claim 12 wherein the complementary first and second mating surfaces include mated tapered joint surfaces.

14. The femoral stem component of claim 12 wherein the flexible shell includes a cross-sectional tripolar scalloped surface shape.

15. The femoral stem component of claim 12 wherein the flexible shell includes a short segment of narrowing proximate the distal pole.

16. The femoral stem component of claim 12 wherein the flexible shell includes a curving arc segment relative to the longitudinal axis.

17. A femoral stem component of a femoral hip prosthesis, suitable for implantation within a human patient, having an anterior surface, a posterior surface, a medial surface, a lateral surface, and a proximal pole generally opposite a distal pole along a longitudinal axis, the prosthesis generally wider medially proximate the proximal pole, the femoral stem component comprising:

a proximal component detachable from and operably interconnectable with a distal component at complimentary first and second mating surfaces;

the proximal component including a centrally located cylindrical bore opening proximate the proximal pole and generally aligned along the longitudinal axis of the prosthesis suitable for slidably and telescopically receiving an aligning rod therethrough, and a first transition portion having a central cavity in open communication with the cylindrical bore proximally, the central cavity generally narrow proximally and widening distally ending proximate the first mating surface proximate a distal end of the proximal component; and the distal component comprising a second transition portion proximal to a flexible shell portion;

the second transition portion including a central cavity with a geometry complimentary to the first transition portion central cavity beginning proximate the second mating surface and extending and widening distally along the longitudinal axis of the prosthesis; and the flexible shell portion including having a centrally located shell cavity in open communication with the second transition portion central cavity, including an opening into the shell cavity proximate the distal pole and a longitudinally oriented slot in open communication with the shell cavity and the opening;

wherein the second transition portion and flexible shell portion provide for the distal component that is substantially flexible relative to the proximal component.

18. The femoral stem component of claim 17 wherein the complementary first and second mating surfaces include mated tapered joint surfaces.

19. The femoral stem component of claim 17 wherein the flexible shell portion includes a cross-sectional tripolar scalloped surface shape.

20. The femoral stem component of claim 17 wherein the flexible shell portion includes a short segment of narrowing proximate the distal pole.

21. The femoral stem component of claim 17 wherein the flexible shell portion includes a curving arc segment relative to the longitudinal axis.

* * * * *

UNITED STATES PATENT AND TRADEMARK OFFICE
CERTIFICATE OF CORRECTION

PATENT NO. : 5,725,595
DATED : March 10, 1998
INVENTOR(S) : Ramon B. Gustilo

It is certified that error appears in the above-indentified patent and that said Letters Patent is hereby corrected as shown below:

Col. 1, line 57, delete "show" and insert therefor -- shown--.

Col. 2, line 1, delete "on" and insert therefor --an alternate--.

Signed and Sealed this

Twenty-sixth Day of May, 1998

Attest:

BRUCE LEHMAN

*Attesting Officer*  *Commissioner of Patents and Trademarks*